United States Patent
Tansley et al.

(10) Patent No.: US 7,798,952 B2
(45) Date of Patent: Sep. 21, 2010

(54) AXIAL FLOW BLOOD PUMP

(75) Inventors: Geoffrey Douglas Tansley, Kegworth (GB); Martin Christopher Cook, Coogee (AU); John Campbell Woodard, Thornleigh (AU)

(73) Assignee: Thoratec Corporation, Pleasanton, CA (US)

( * ) Notice: Subject to any disclaimer, the term of this patent is extended or adjusted under 35 U.S.C. 154(b) by 869 days.

(21) Appl. No.: 10/575,118

(22) PCT Filed: Oct. 8, 2004

(86) PCT No.: PCT/AU2004/001379

§ 371 (c)(1),
(2), (4) Date: Jan. 29, 2007

(87) PCT Pub. No.: WO2005/032620

PCT Pub. Date: Apr. 14, 2005

(65) Prior Publication Data

US 2007/0276480 A1 Nov. 29, 2007

(30) Foreign Application Priority Data

Oct. 9, 2003 (AU) .............................. 2003905511

(51) Int. Cl.
*A61M 1/12* (2006.01)
(52) U.S. Cl. ........................................................ 600/16
(58) Field of Classification Search ............... None
See application file for complete search history.

(56) References Cited

U.S. PATENT DOCUMENTS

| 4,382,199 A | 5/1983 | Isaacson |
| 4,688,998 A | 8/1987 | Olsen et al. |
| 4,817,586 A | 4/1989 | Wampler |
| 4,906,226 A | 3/1990 | Hecker et al. |
| 4,944,748 A | 7/1990 | Bramm et al. |
| 4,995,857 A | 2/1991 | Arnold |
| 5,055,005 A | 10/1991 | Kletschka |
| 5,078,741 A | 1/1992 | Bramm et al. |
| 5,112,200 A | 5/1992 | Isaacson et al. |
| 5,195,877 A | 3/1993 | Kletschka |
| 5,211,546 A | 5/1993 | Isaacson et al. |
| 5,289,821 A | 3/1994 | Schwartz |
| 5,326,344 A | 7/1994 | Bramm et al. |

(Continued)

FOREIGN PATENT DOCUMENTS

CA 2237203 3/1998

(Continued)

OTHER PUBLICATIONS

PCT International Search Report dated Dec. 1, 2004.

(Continued)

*Primary Examiner*—Kennedy J Schaetzle
(74) *Attorney, Agent, or Firm*—Squire, Sanders & Dempsey L.L.P.

(57) ABSTRACT

An axial flow rotary blood pump including an impeller (5) adapted to be magnetically rotated within a housing by the interaction of magnets disposed on or in the impeller and stators disposed on or in the housing. The impeller includes at least one support ring (2) supporting a plurality of blades (4), and a hydrodynamic bearing (3) that operates at least axially and radially in respect of an axis of rotation of the impeller (5).

20 Claims, 8 Drawing Sheets

U.S. PATENT DOCUMENTS

| | | | |
|---|---|---|---|
| 5,370,509 A | 12/1994 | Golding et al. | |
| 5,385,581 A | 1/1995 | Bramm et al. | |
| 5,470,208 A | 11/1995 | Kletschka | |
| 5,685,700 A | 11/1997 | Izraelev | |
| 5,695,471 A | 12/1997 | Wampler | |
| 5,840,070 A * | 11/1998 | Wampler | 604/131 |
| 5,924,848 A | 7/1999 | Izraelev | |
| 5,938,412 A | 8/1999 | Izraelev | |
| 6,027,498 A | 2/2000 | Mutch et al. | |
| 6,053,705 A | 4/2000 | Schob et al. | |
| 6,066,086 A | 5/2000 | Antaki et al. | |
| 6,071,093 A | 6/2000 | Hart | |
| 6,080,133 A | 6/2000 | Wampler | |
| 6,100,618 A | 8/2000 | Schoeb et al. | |
| 6,120,537 A | 9/2000 | Wampler | |
| 6,158,984 A | 12/2000 | Cao et al. | |
| 6,171,078 B1 | 1/2001 | Schob | |
| 6,206,659 B1 | 3/2001 | Izraelev | |
| 6,217,541 B1 | 4/2001 | Yu | |
| 6,227,797 B1 * | 5/2001 | Watterson et al. | 415/107 |
| 6,234,772 B1 | 5/2001 | Wampler et al. | |
| 6,234,998 B1 | 5/2001 | Wampler | |
| 6,250,880 B1 | 6/2001 | Woodward et al. | |
| 6,264,635 B1 | 7/2001 | Wampler et al. | |
| 6,277,078 B1 | 8/2001 | Porat et al. | |
| 6,368,083 B1 | 4/2002 | Wampler | |
| 6,609,883 B2 | 8/2003 | Woodard et al. | |
| 6,688,861 B2 | 2/2004 | Wampler | |
| 6,866,625 B1 | 3/2005 | Ayre et al. | |
| 6,966,748 B2 | 11/2005 | Woodward et al. | |
| 7,052,253 B2 | 5/2006 | Izraelev | |
| 7,070,398 B2 | 7/2006 | Olsen et al. | |
| 2001/0009645 A1 | 7/2001 | Noda | |
| 2002/0183628 A1 | 12/2002 | Reich et al. | |
| 2004/0084398 A1 | 5/2004 | Breitschwerdt et al. | |
| 2004/0084399 A1 | 5/2004 | Cook et al. | |
| 2004/0234397 A1 | 11/2004 | Wampler | |
| 2007/0231135 A1 | 10/2007 | Wampler et al. | |
| 2008/0080983 A1 | 4/2008 | Wampler et al. | |
| 2008/0085184 A1 | 4/2008 | Wampler et al. | |
| 2008/0089779 A1 | 4/2008 | Wampler et al. | |
| 2008/0089797 A1 | 4/2008 | Wampler et al. | |

FOREIGN PATENT DOCUMENTS

| | | |
|---|---|---|
| EP | 1 354 606 | 10/2003 |
| JP | 2002-224066 | 8/2002 |
| JP | 2004-278375 | 10/2004 |
| WO | WO 92/15239 | 9/1992 |
| WO | WO 97/29795 | 8/1997 |
| WO | WO 01/12070 | 2/2001 |
| WO | WO 03/015609 | 2/2003 |
| WO | WO 2004/028593 | 4/2004 |

OTHER PUBLICATIONS

Translation of Japanese Notification of Reason for Refusal issued by JPO on Aug. 6, 2009, in connection with Appl. No. 2006-529462, 4 pgs.

International Search Rep. for PCT/AU2004/000829, mailed Aug. 17, 2004, 7 pgs.

* cited by examiner

AXIAL FLOW BLOOD PUMP

FIELD OF THE INVENTION

The present invention relates to improvements in implantable axial flow rotary blood pumps.

BACKGROUND OF THE INVENTION

Cardiovascular disease remains a leading cause of death in the developed world, responsible for more than 40% of deaths in Australia and in the United States. Annual diagnoses of new cases of heart failure in the United States have reached 550,000, leading to a population of approximately 4.7 million people afflicted by the disease; annual cost estimates for heart failure treatment range from USD$10 billion to $38 billion. Cardiac transplantation provides substantial benefit for patients with severe heart failure, however there is a gross disparity between the numbers of potential recipients (800,000 p.a. worldwide) and suitable transplant donors, approximately 3,000 p.a. worldwide. Consequently, there is a clear need for development of an effective heart support device.

In the past, Ventricular Assist Devices ('VADs') or Left Ventricle Assist Devices ('LVADs') have been developed to provide support to the heart and are typically used for temporary (bridge-to-transplant and bridge-to-recovery) and permanent (alternative-to-transplant) support of patients. Generally, support for the left ventricle with an assist device (rather than a total artificial heart) is sufficient to restore cardiovascular function to normal levels for patients with terminal congestive heart failure. As a consequence of the shortage of transplants, there is a focus on long term alternative-to-transplant support in device development. The initial VADs developed were pulsatile (implanted and external to the body) and these have demonstrated enhanced survival and quality of life for patients with end-stage heart failure compared with maximal medical therapy. However these devices are generally large, cumbersome, inefficient, prone to mechanical failure and costly.

It has been noted that continuous flow rotary VADs are generally simpler, smaller and more reliable, as well as cheaper to produce, than the earlier pulsatile systems. For this reason, continuous flow centrifugal devices, such as the VentrAssist™ LVAD, have emerged as the definitive forms of technology in the field of cardiac assistance.

A prior art implantable axial flow rotary blood pump is described in U.S. Pat. No. 5,370,509—Golding et al. This pump includes two blade sets and a support ring. The primary blade set functions as a thrust bearing to pump the blood directly from the inlet to the outlet. The secondary blade set functions to divert blood around the outer surface of the impeller. This diversion of blood is forced through a radially extending restriction. The effect of which is to create a fluid bearing that suspends the impeller only in the axial direction. The pump disclosed within this document has two main disadvantages.

The first disadvantage is that the blood paths disclosed in that document are not perfected. The subsidiary blood flow around the impeller is pushed in the same direction as the primary blood flow through the middle of the impeller. This type of blood path requires relatively high energy to maintain and generally lacks efficiency.

The second disadvantage is that secondary blade set may induce thrombogenesis and/or haemolysis within the pump due their shape.

Another prior art pump is disclosed in U.S. Pat. No. 6,227,797—Watterson et al. It is a centrifugal rotary blood pump with a hydrodynamically suspended impeller. The main disadvantage with this device is that the impeller of this pump includes complex blade geometry which increases the cost of manufacturing.

U.S. Pat. No. 5,211,546—Isaacson et al., discloses an axial flow rotary blood pump wherein the impeller is only hydrodynamically suspended in the radial direction relative to the axis of rotation. Additionally, the pump disclosed therein includes a hub or spider to position the impeller. Hubs and spiders typically generate a location within the pump of blood flow stagnation. Locations or points of stagnation within the channel of blood flow should net be avoided to reduce the chance or likelihood of thrombogenesis or blood clots.

U.S. Pat. No. 6,100,618—Schoeb et al. describes an axial flow pump with a simplifier motor rotor design. This pump is not suitable as an implantable blood pump design and the impeller within the pump is only radially hydrodynamically suspended.

It is an object of the present invention to address or ameliorate one or more of the abovedescribed problems of the prior art.

BRIEF DESCRIPTION OF THE INVENTION

In a first aspect the present invention consists in an axial flow rotary blood pump including an impeller adapted to be magnetically rotated within a housing by the interaction of magnets disposed on or in the impeller and stators disposed on or in the housing, characterised in that said impeller includes at least one support ring supporting a plurality of blades, and a hydrodynamic bearing that operates at least axially and radially in respect of an axis of rotation of the impeller.

Preferably said hydrodynamic bearing exclusively suspends said impeller within a cavity.

Preferably said hydrodynamic bearing is formed by angular pads.

Preferably said support ring includes the hydrodynamic bearing.

Preferably said support ring includes the magnets.

Preferably said plurality of blades extend from the support ring towards the centre of the pump.

Preferably said the blades have a decreasing pitch to straighten blood flowing out of the pump.

Preferably said pump is spider-less and sealless.

Preferably said impeller, when in use, experiences retrograde blood flow around its periphery.

BRIEF DESCRIPTION OF THE DRAWINGS

Embodiments of the present invention will now be described with reference to the accompanying drawings wherein.

BRIEF DESCRIPTION OF THE PREFERRED EMBODIMENTS

The pump assemblies according to various preferred embodiments to be described below, all have particular, although not exclusive, application for implantation within a patient. In particular, these pump assemblies may be used to reduce the pumping load on a patient's heart to which the pumping assembly is connected. There may be other applications suitable for use with embodiments of the present invention and these may include use as: perfusion pumps, applications requiring the pumping of fragile fluids, external short term surgical blood pumps, and/or long term implantable blood pumps.

In practice, the preferred embodiments of the present invention may be performed by placing the blood pump entirely within the patient's body and connecting the pump between the apex of the left ventricle of the patient's heart and the ascending aorta so as to assist left side heart function. It may also be connected to other regions of the patient's circulation system including: the right side of the heart and/or distal regions of a patient such as the femoral arteries or limbs.

Figure 1:
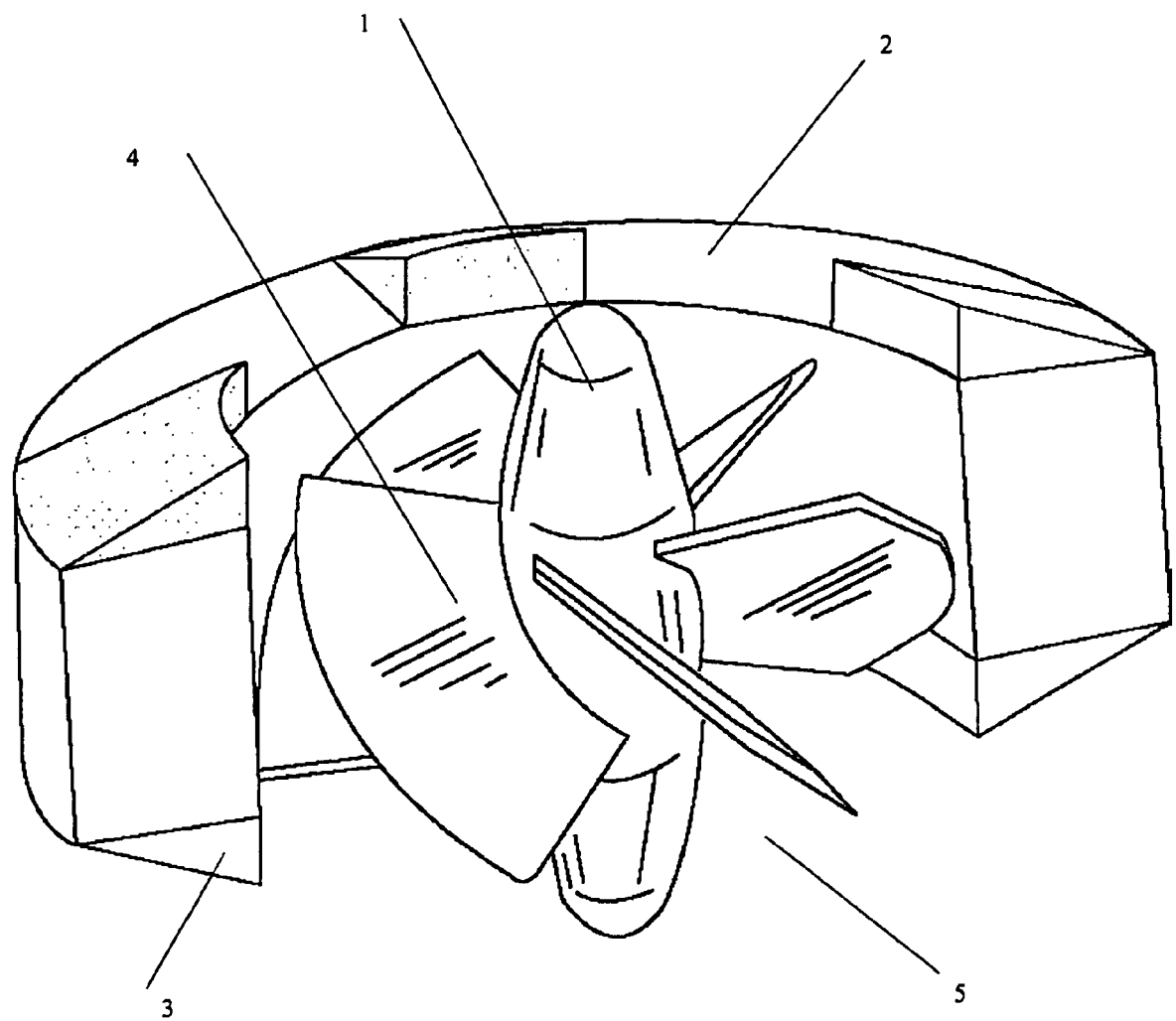
FIG. 1 is a perspective and cross-sectional view of a first preferred embodiment of the present invention.
Figure 2:
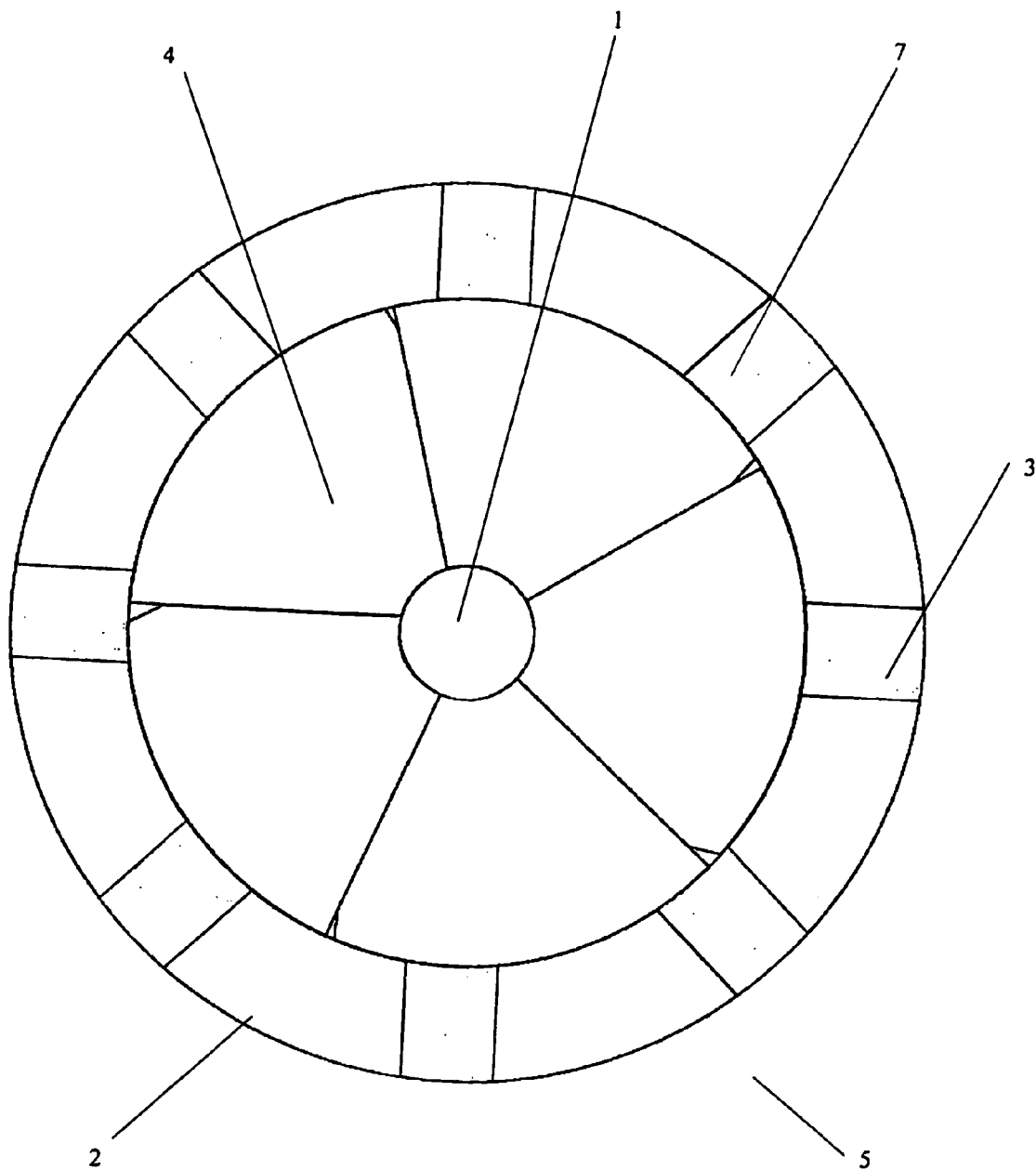
FIG. 2 is a top view of the first embodiment shown in FIG. 1.
Figure 3:
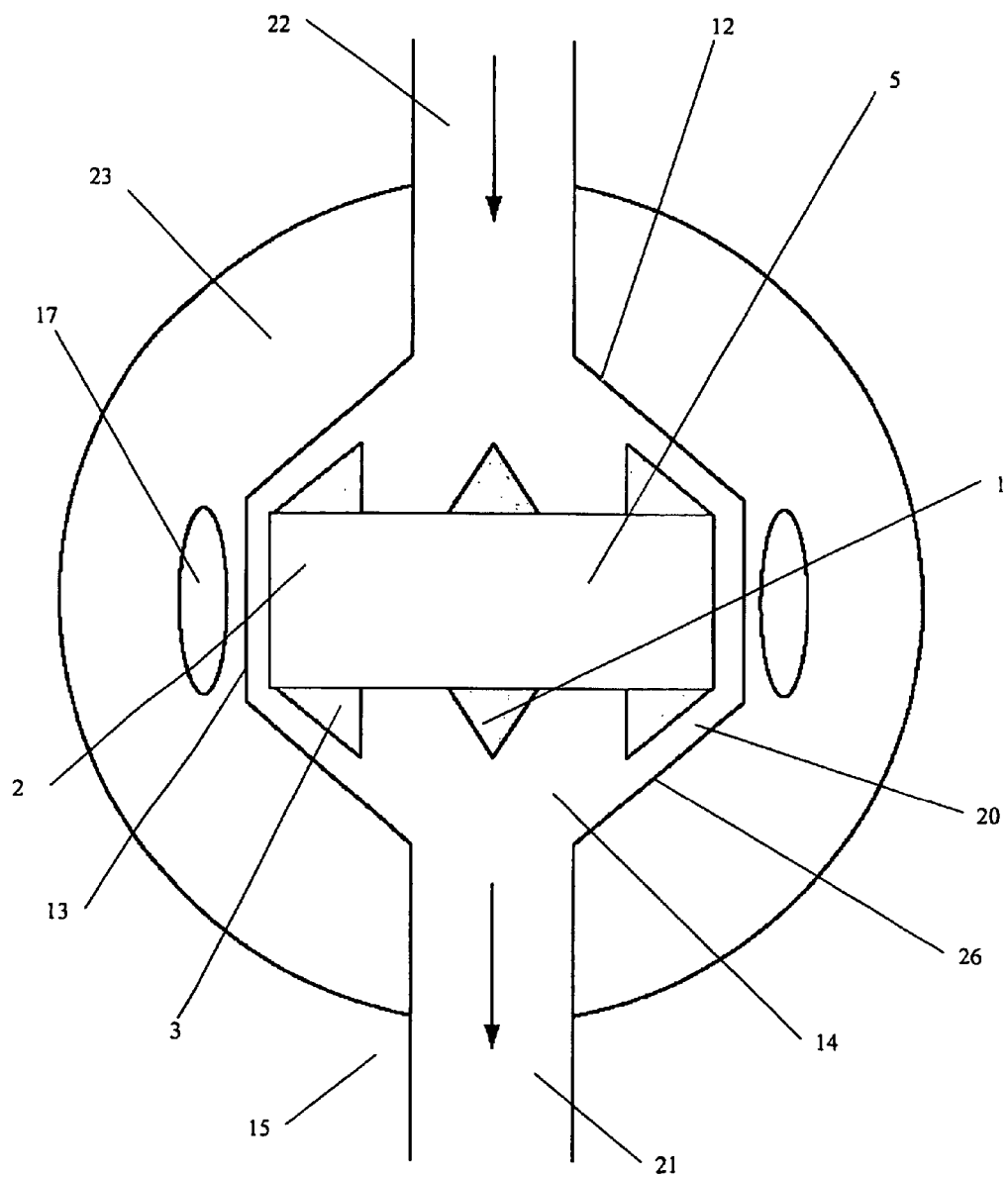
FIG. 3 is a cross sectional view of the first embodiment.
Figure 4:
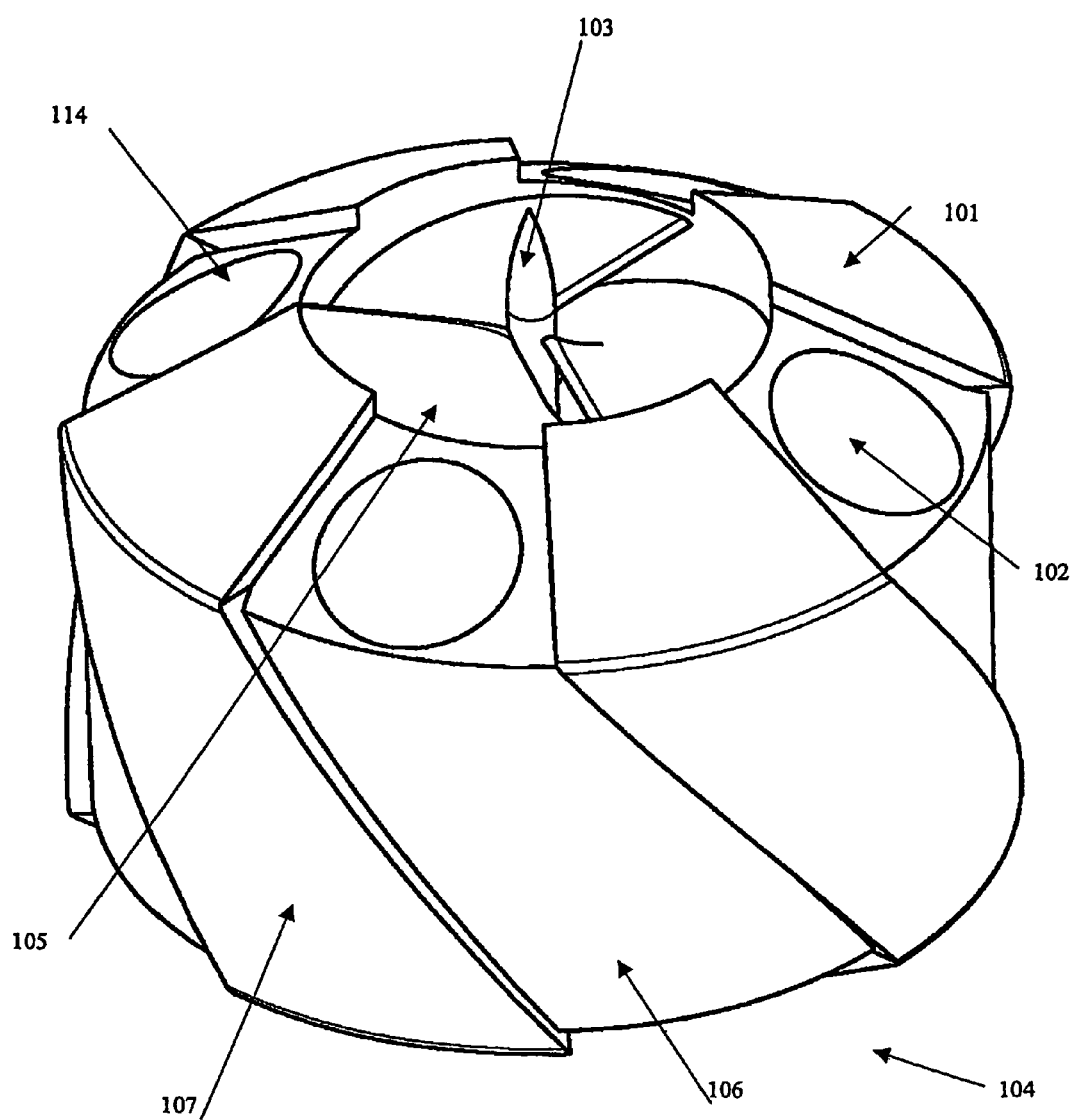
FIG. 4 is a perspective view of a second embodiment.
Figure 5:
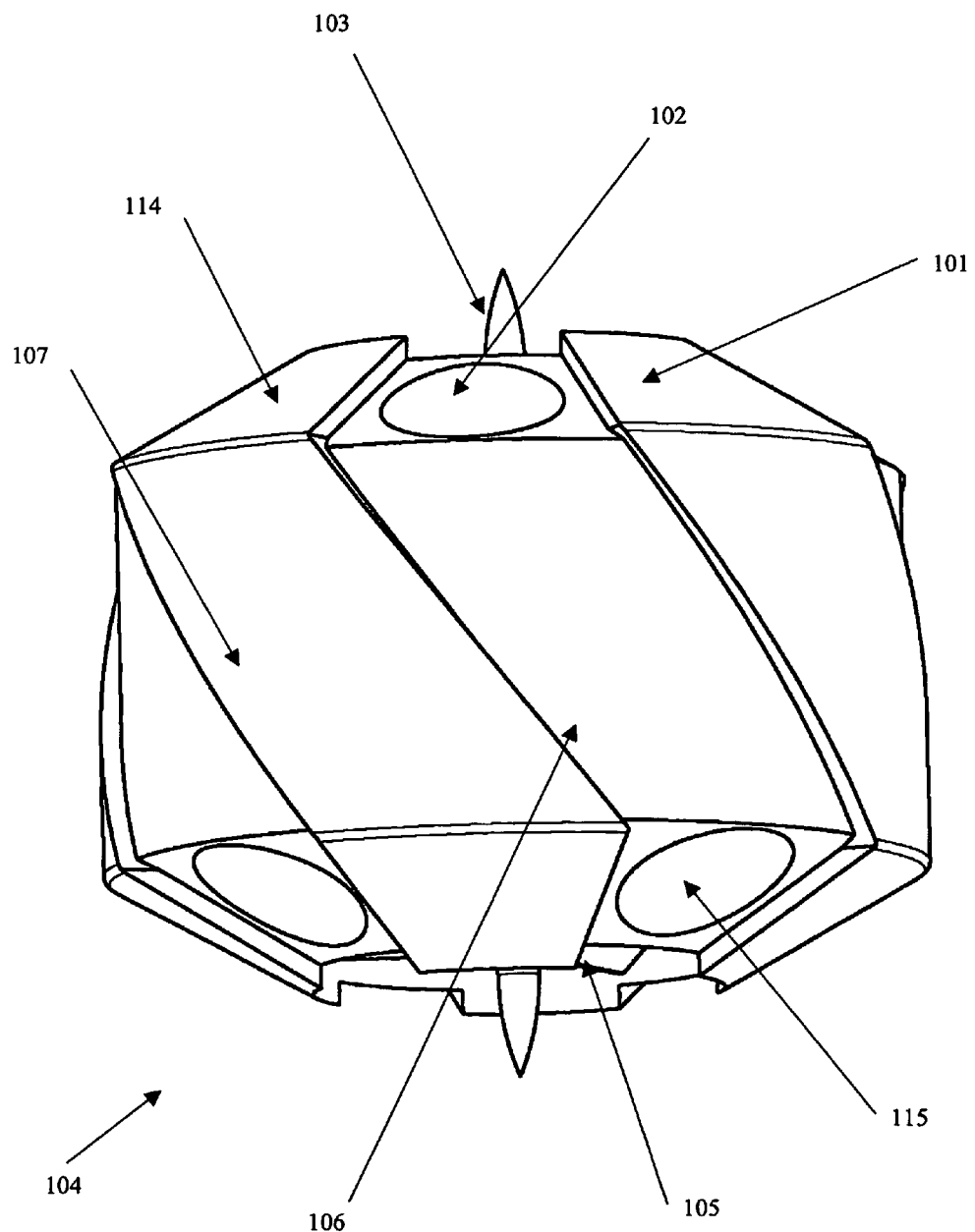
FIG. 5 is a side view of the second embodiment shown in FIG. 4.
Figure 6:
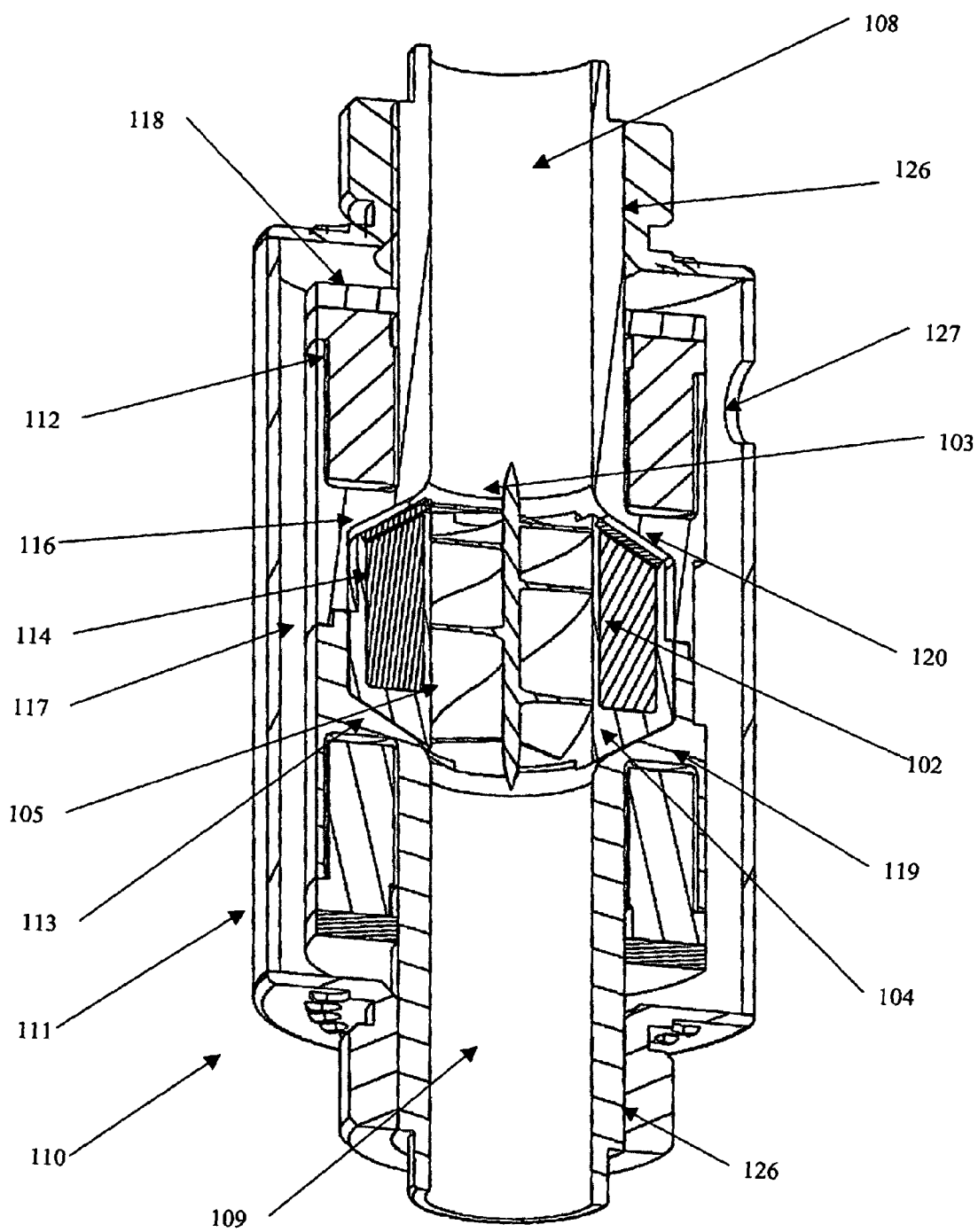
FIG. 6 is a cross-sectional view of the second embodiment.
Figure 7:
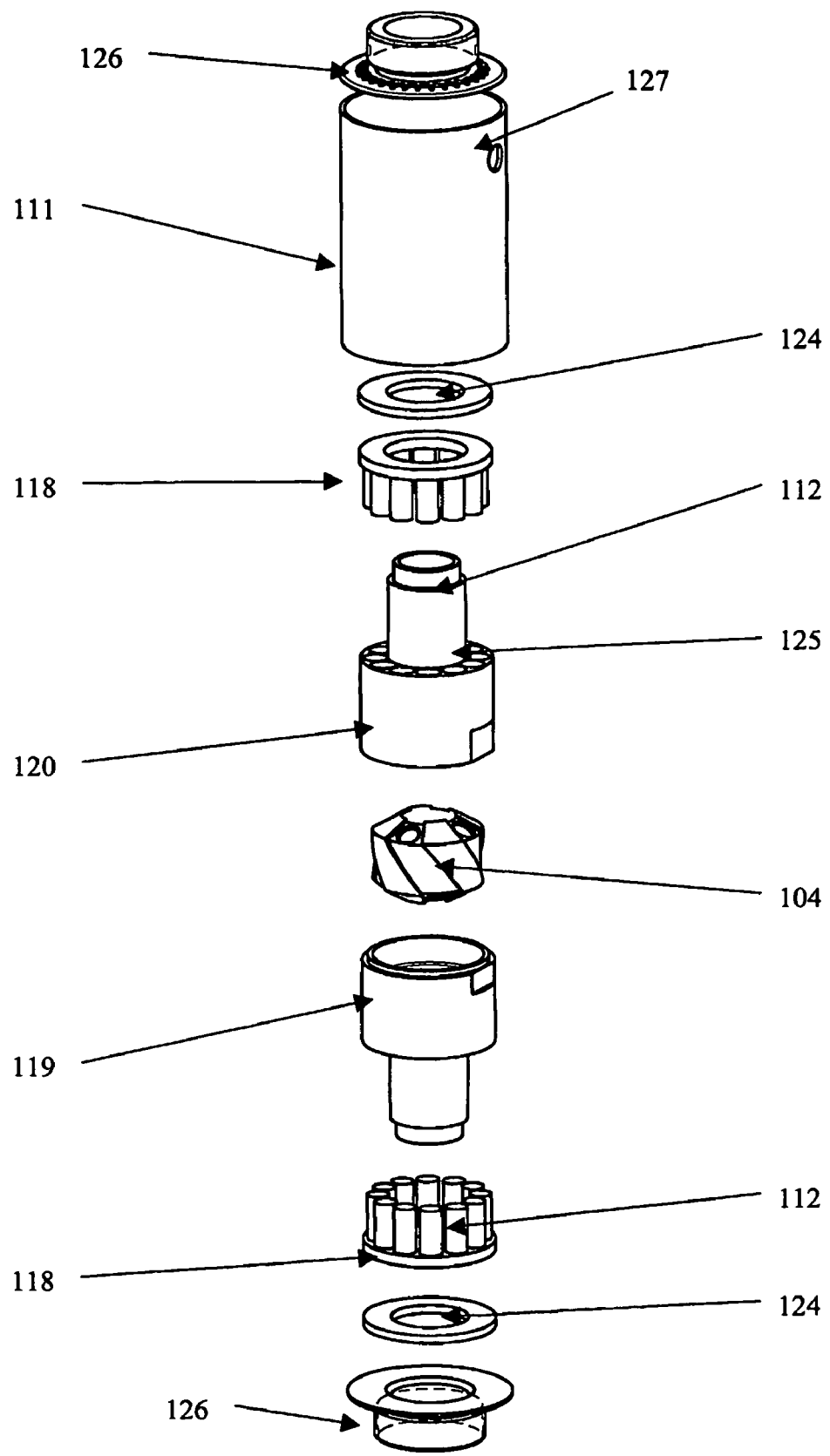
FIG. 7 shows an exploded perspective view of the second embodiment.

In a first preferred embodiment depicted in FIGS. 1, 2 & 3, the blood pump 15 includes an impeller 5 which is fully sealed within the pump body or housing 23. The impeller 5 has five spaced apart blades 4, extending from a central shaft 1, and connected to a support ring 2.

Preferably the impeller 5 is urged to rotate, in use, by an electric motor. In a preferred embodiment, the electric motor may include several sets of electrical coils or stators 17 mounted on or about the housing 23 and a plurality of permanent magnets 7 embedded or encased within the blades 4 of the impeller 5. When in operation, the electric coils sequentially energise and exert an electromagnetic force on the impeller 5 and the permanent magnets 7. If the pump is properly configured, the sequential energising of the electric coils or stators 17 will cause the impeller 5 to rotate. The electric coils or stators 17 may be mounted in an axial and/or radial orientation, in relation to the axis of rotation of the impeller.

When the impeller 5 is rotated, the blades 4 push a fluid, for example blood, in an axial direction relative to the axis of rotation of the impeller 5 and generally towards an outlet 21. The support ring 2 has a generally rectangular cross section excluding the portions which form the hydrodynamic bearings 3. The generally rectangular cross section allows square or rectangular cross-section permanent magnets 7 to be easily inserted within the support ring 2. The benefit is that it is easier to manufacture magnets in a square or rectangular cross-section shape than more complex shapes as provided by in the prior art. The support ring 2 may also be of hollow construction to minimise weight and/or to reduce complexity of construction.

The impeller 5 includes four hydrodynamic bearings 3. The surface of hydrodynamic bearings 3 is generally angled between 0° and 90° relative to the axis of rotation so as to cooperate with an inner surface of the housing 23 to generate a hydrodynamic force away from the inner surface of the cavity 14. The combined effect of these hydrodynamic bearings 3 is to hydrodynamically suspend the impeller 5 within the housing 23, when in use. The most preferred angle for the hydrodynamic bearings 3 is approximately 45°. These hydrodynamic bearings 3 produce axial and radial component vectors. Preferably, the hydrodynamic bearings 3 supply at least an axial component vector to suspend the impeller 5 in an axial direction, which is generally parallel to the axis of rotation of the impeller 5.

Four spaced apart permanent magnets 7 are embedded within the support ring 2 of the impeller 5. Whilst the permanent magnets 7 may be placed in any location within the support ring 2, the most optimal positions for the permanent magnets 7 are shown in FIG. 2. It may be important to balance the positions of the magnets to increase impeller stability and balance.

The hydrodynamic bearings 3 are mounted on the upper surface and the lower surface of the support ring 2. These hydrodynamic bearings 3 provide a zero net thrust force which is capable of hydrodynamically suspending the impeller 5 in the pump housing 23, when in use. The hydrodynamic bearings 3 may also be used in conjunction with other bearings means such as magnetic bearings.

The blood pump 15 includes an inlet 22 and an outlet 21 formed in housing 23. Between the inlet 22 and the outlet 21 is pumping cavity 14, which allows fluid communication throughout the pump, when in use. Impeller 5 rotates within cavity 14 and its blades 4 supply pumping motion to the blood, to be pumped when in use.

The housing 23 includes machined surface on the wall of the cavity 14. This machined surface may include an upper inner surface 12, middle inner surface 13 and a lower inner surface 26. The upper inner surface 12, middle inner surface 13 and/or the lower inner surface 26 cooperate with at least a portion of outer surfaces of the impeller 5 to form, in effect, hydrodynamic bearings 3. In particular, these portions of the surfaces include the outer surface of the support ring 2 and/or the hydrodynamic bearings 3 mounted on the support ring 2.

When impeller 5 is rotated, the hydrodynamic bearings 3 may preferably cooperate with a proximate portion of the angular inner surfaces 12 & 26 of the cavity 14. Thereby, when blood passes through a gap 20 located between the hydrodynamic bearing 3 and inner surface 26 of the cavity 14, the impeller 5 experiences a hydrodynamic thrust force. This thrust force acts upon the impeller 5 in a direction away from the inner walls of the housing 23. The net force of all of the hydrodynamic bearings 3 may result in the impeller 5 being partially or exclusively hydrodynamically suspended within the cavity 14.

The blood pump 15 of the first embodiment is in an axial flow configuration. The impeller 5, in use, is magnetically urged to rotate by the electro-magnetic interaction between permanent magnets 7 embedded or encased within the support ring 2 and the electromagnetic coils forming stators 17 mounted in a radial orientation in respect the axis of rotation of the impeller 5. Preferably, there are three electric coils forming stators 17, however the number of coils may be amended without generally affecting the functionality of this embodiment, so long as there are at least two coils. It should be noted that other coil configurations may also be used and these configurations may include axial mounting configurations.

The hydrodynamic bearings 3 have a generally wedge shaped side profile so as to generate a hydrodynamic force when rotated within the complementary shaped cavity 14. Please note that the number and size of the hydrodynamic bearings 3 may be also amended without departing from the scope of the present invention. Other configurations of hydrodynamic bearings 3 may include one hydrodynamic bearing mounted on each side of the impeller 15 and the bearing may run along the entire length of the support ring 2.

The hydrodynamic bearings 3 may be constructed to balance the hydrodynamic thrust forces and to suspend the impeller 5 away from the inner surfaces of the cavity 14.

The impeller 5 includes at least an axial and a radial component to the hydrodynamic thrust force generated by the angular surface of the hydrodynamic bearings 3. The hydrodynamic force imparted, in the preferred embodiment, acts simultaneously in both an axial and radial direction with respect to the orientation of the impeller 5.

It is important to note that in order to function safely and reliably, when in use, preferred embodiments of the present invention will include features that limit thrombogenesis and haemolysis and which add to the mechanical reliability of the pump. Preferably, the impeller of the preferred embodiments may include at least some amount of dimensional stability to prevent the blades and/or impeller changing their shape or configuration, in situ. Small dimensional changes in the shape or configuration of impeller 5 or housing 23 may occur due to warping or twisting through regularly use of the pump. Dimensional stability is generally increased or improved by the inclusion of support structures particularly in regard to the impeller 5. These support structures may include the support ring 2.

The impeller 5 may also include increased dimensional stability, which is supplied by the generally square or rectangular cross-section of the support ring 2. The support ring 2 is joined to the blades 4 in this configuration to prevent or limit the amount or severity of twisting, warping and/or other undesirable dimensional deformation.

The shaft 1 is preferably centered within the periphery of the impeller 5 and is orientated in an axial direction. The blades 4 of this first embodiment are generally thin and arcuate in shape and may incorporate features to minimise drag and/or shear forces.

The first embodiment preferably operates at speeds of between 1500 rpm to 4000 rpm. The preferred outer blade diameter is 40 mm, outer housing average diameter is 60 mm and the housing axial length is 44 mm.

In FIGS. 4, 5, 6, 7 & 8, a second embodiment of the present invention is shown. An impeller 104 is provided for by the embodiment and includes a central shaft 103 and a support ring 114. Extending from the internal or interior surface of the support ring 114 towards the centre of the pump 110 are a plurality or set of blades 105. In this preferred embodiment, three blades comprise the said blade set 105. However any number of individual blades may be used to construct the blade set 105.

The blades 105 fully extends from the support ring 114 to abut against the central shaft 103.

The support ring 114 preferably includes: two sets of permanent magnets 102 & 115; hydrodynamic bearing surfaces 101 and channels 106 formed between the hydrodynamic bearing surfaces 101.

The upper set of permanent magnets 102 extend from the base of the channels 106 in the upper surface into the support ring 114. In this embodiment, the upper set of permanent magnets 102 comprise four permanent magnets aligned as to have the northern pole of the magnets facing up. Preferably, the upper set of permanent magnets 102 extends almost throughout the entire width of the support ring 114 without interfering with the hydrodynamic bearing surface 101 on the lower side of the support ring 114. The lower set of permanent magnets 115 works in an inverse manner to the upper set of permanent magnets 102. The northern pole of the lower set of permanent magnets 115 faces downwards. The permanent magnets are disposed alternately in respect of polarity and are spaced at 45° intervals. The permanent magnets 102 & 115 are jacketed beneath a thin layer of impermeable biocompatible material to prevent corrosion or bio-toxic leaking.

This embodiment includes an impeller 104, which is designed to be rotated clockwise, with four hydrodynamic bearing surfaces 101. The hydrodynamic bearing surface 101 forms a pad which covers the upper face of the support ring 114 and extends downwardly and at an anti-clockwise angle to the lower face of the support ring 114. The angular extension 107 of the hydrodynamic bearing surface 101 may generate a hydrodynamic bearing that is capable of acting at least axially and/or radially in respect of the axis of rotation of the impeller 104. The hydrodynamic bearing may also act in respect of other degrees of freedom.

Each hydrodynamic bearing surface 101 includes a leading edge and a trailing edge. The leading edge is the edge that leads the trailing edge when the impeller is rotated in a clockwise direction. Preferably, the leading edge is 50 µm lower than the trailing edge. The angularly surface cooperates with the interior of the pump housing to form a restriction. This restriction generates a thrust force perpendicular to the bearing surface. When the impeller 104 is in use, the hydrodynamic bearings suspend the impeller 104 within the pump housing 120. The hydrodynamic bearing surfaces 101 have a generally wedge shaped appearance.

The channels 106 are approximately 0.5 mm deeper than the leading edge of the hydrodynamic bearing. This channel 106 may allow retrograde blood flow over the surface of the impeller 104, when in use. This is described in greater detail further on in this specification.

The pump 110 pumps blood from the inlet 108 to the outlet 109 by the rotation of impeller 104, which in turn rotates a plurality of blades 105. The impeller is mounted within an upper 120 and lower housing 119. The housings 120 & 119 are preferably joined by laser welding at location 117. When in use, the impeller 104 is urged to rotate magnetically through the synchronised activation of the stators 112 cooperating with the permanent magnets 102. The preferred speed of rotation of impeller 104 is approximately 2,000 rpm. However, it will be appreciated that small changes in shape and diameter of impeller 104 will greatly effect the preferred speed of rotation.

Preferably, the internal portions of the pump 110 are encapsulated within a casing shell 111 and two end caps 126. The end caps 126 and casing shell 111 may be constructed of a biocompatible Titanium alloy which may be joined and sealed by laser welding. It includes a casing shell hole 127 to allow access to the interior of the pump by electronic leads for pump control, power and data.

Each blade 105 forms a screw thread configuration around the central shaft 103. The pitch of the screw thread of the individual blades decreases as the blade extends away form the inlet of the pump 110. This allows some the torsional force applied to the blood being pumped to be translated into thrust in the direction of the outlet and straightens the flow of blood leaving the pump. Preferably, using this type of configuration may reduce or eliminate the need for flow straighteners in the outflow of the pump 110.

The retrograde blood flow in the pump 110, has an elevated pressure in outlet 109 when compared to the pressure level in the inlet 108 as a result of the rotation of impeller 104. The pressure differential created between the outlet 109 and inlet 104 means that blood will, where possible, attempt to flow back to the inlet 104. The blood is purposively given an opportunity to do this by the gap 113 which occurs between the outermost surface of the impeller 104 and the innermost surface of the housings 119 & 120, which forms a cavity 116 for the impeller 104 to rotate within. The gap 113 is the location where a hydrodynamic bearing is created by the interaction of the hydrodynamic bearing surfaces 101 and the walls of the cavity 116. Preferably the gap 113 is approximately 80 μm. The gap 113 is preferably small enough so as exclude a majority of blood cells from this area by fluid forces. This exclusion of red blood cells reduces haemolysis caused by the bearing forces. Additionally, the constant flow of fresh blood across the outermost surfaces of the impeller 104 reduces the chance or likelihood of thrombogenesis in the vicinity of the impeller 104.

The stators 112 are in an axial configuration around the impeller 104 and are formed from twelve independent coils mounted directly onto a printed circuit board 118. When the pump 110 is assembled, the coils are inserted within twelve wells 125 formed in the outer surface of the housing 120. The printed circuit board 118 forms part of the control system for the pump 110 and is backed by an iron metal yoke to improve EMF efficiency.

Figure 8:
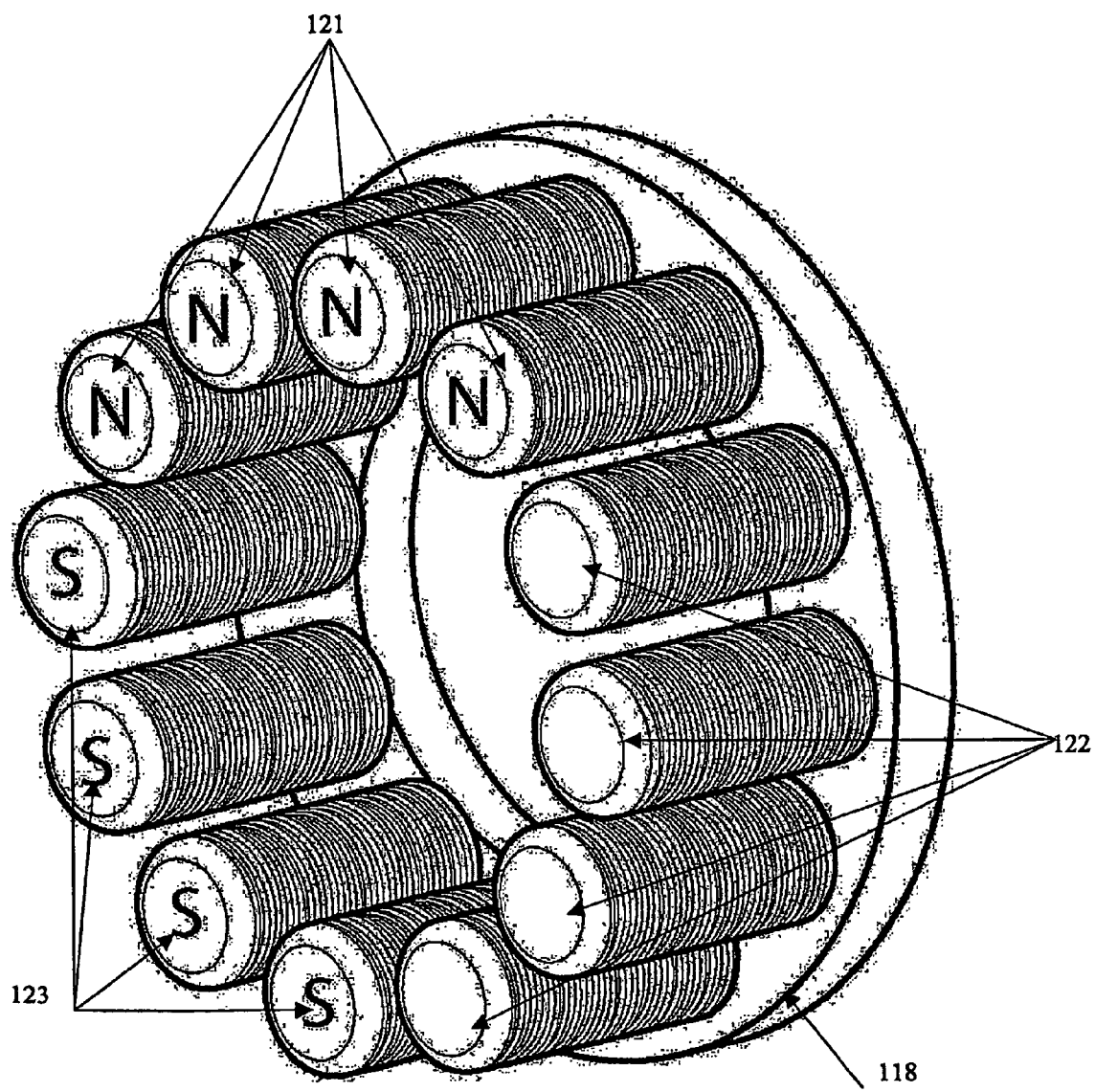
FIG. 8 shows an enlarged and rotated view of a portion of the second embodiment.

In FIG. 8, the twelve stator coils are shown at one instance in time when the coils are firing to urge the impeller 104. The twelve stator coils are depicted in three groups 121, 122 & 123. The three groups of coils 121, 122, & 123 cooperate with the permanent magnets 102 & 115 of the impeller 104 to rotate it. In the instance shown, the first group of coils 121 have their north poles distal from the printed circuit board 118. The second group of coils 123 have an inverted polarity and the third polarity is not charged. The charging sequence of the groups of coils 121, 122, & 123 rotates clockwise and induces the rotation of the impeller 104.

An advantage of both the abovementioned embodiments over the prior art is that the manufacture of impellers 5 and 104 is a separate machining operation to that of the respective support rings 2 and 114. As the magnets are carried by the support rings 2 and 114 and not the blades of the impeller 5 and 104 is of less complexity and therefore less expensive manufacture than that employed in prior art blood pumps with hydrodynamic bearings where the magnets are encapsulated within the blades.

The above descriptions only describe some of the embodiments of the present inventions and modifications. It may be obvious to those skilled in the art that further modifications can be made thereto without departing from the scope and spirit of the present invention.

The invention claimed is:

1. An axial flow rotary blood pump including an impeller adapted to be magnetically rotated within a housing by the interaction of magnets disposed on or in the impeller and stators disposed on or in the housing, wherein the impeller includes a central shaft, a support ring, and a plurality of spaced apart blades extending between the support ring and the central shaft, wherein the support ring forms at least two surfaces extending at an angle to an axis of rotation for the impeller to form hydrodynamic bearing surfaces and a channel disposed between the at least two surfaces.

2. The axial flow rotary blood pump of claim 1, wherein each of the at least two surfaces extends, in a radial direction, between a leading edge and a trailing edge, and the leading edge is lower than the trailing edge.

3. The axial flow rotary blood pump of claim 2, wherein the leading edge is 50 μm lower than the trailing edge.

4. The axial flow rotary blood pump of claim 1, wherein each of the at least two surfaces extend to a leading edge formed so that a first portion of the leading edge proximal an upper face of the support ring is radially offset, with respect to the axis of rotation, from a second portion of the leading edge proximal a lower face of the support ring.

5. The axial flow rotary blood pump of claim 1, wherein the magnets disposed on or in the impeller include an upper set of magnets and a lower set of magnets radially offset from the upper set of magnets.

6. The axial flow rotary blood pump of claim 1, wherein the support ring forms four surfaces extending at the angle, wherein the four surfaces oppose walls of the housing to thereby form a space for a hydrodynamic bearing.

7. The axial flow rotary blood pump of claim 1, wherein a gap is formed between the channel and a surface of the housing at an outlet end of the impeller to allow blood to flow from the outlet end of the impeller to an input end thereof so that the impeller, when in use, experiences retrograde blood flow around its periphery.

8. The axial flow rotary blood pump of claim 1, wherein the stators are axially offset from the magnets.

9. An axial flow rotary blood pump including an impeller adapted to be magnetically rotated within a housing by the interaction of magnets disposed on or in the impeller and stators disposed on or in the housing, characterized in that the impeller includes at least one support ring supporting a plurality of blades, and a hydrodynamic bearing that operates at least axially and radially in respect of an axis of rotation of the impeller, wherein the blades have a decreasing pitch to straighten blood flowing out of the housing.

10. An axial flow rotary blood pump including an impeller adapted to be magnetically rotated within a housing by the interaction of magnets disposed on or in the impeller and stators disposed on or in the housing, characterized in that the impeller includes at least one support ring supporting a plurality of blades, and a hydrodynamic bearing that operates at least axially and radially in respect of an axis of rotation of the impeller, wherein the housing is spider-less and seal-less.

11. An axial flow rotary blood pump including: an impeller adapted to be magnetically rotated within a housing by the interaction of magnets disposed on or in the impeller and stators disposed on or in the housing, wherein the impeller includes at least one hydrodynamic thrust bearing and blades having a decreasing pitch to straighten blood flowing out of the housing.

12. The axial flow rotary blood pump of claim 11, wherein the impeller further includes a support ring forming at least two surfaces extending at an angle to an axis of rotation for the impeller to form hydrodynamic bearing surfaces and a channel disposed between the at least two surfaces.

13. The axial flow rotary blood pump of claim 12, wherein each of the at least two surfaces extends, in a radial direction, between a leading edge and a trailing edge, wherein the leading edge is lower than the trailing edge.

14. The axial flow rotary blood pump of claim 12, wherein each of the at least two surfaces extend to a leading edge formed so that a first portion of the leading edge proximal an upper face of the support ring is radially offset, with respect to the axis of rotation, from a second portion of the leading edge proximal a lower face of the support ring.

15. The axial flow rotary blood pump of claim 12, wherein the magnets disposed on or in the impeller include an upper set of magnets and a lower set of magnets radially offset from the upper set of magnets.

16. The axial flow rotary blood pump of claim 12, wherein the support ring forms four surfaces extending at the angle and opposing walls of the housing.

17. The axial flow rotary blood pump of claim 11, wherein the blades form a screw thread configuration about a central shaft of the impeller.

18. The axial flow rotary blood pump of claim 17, wherein downstream of the impeller the axial flow rotary blood pump is devoid of flow straighteners.

19. The axial flow rotary blood pump of claim 11, wherein an outlet for the axial flow rotary blood pump is configured so that a net flow direction at the outlet is substantially parallel to an axis of rotation for the impeller.

20. The axial flow rotary blood pump of claim 11, wherein the stators are axially offset from the magnets.

* * * * *